(12) United States Patent
Yamaguchi et al.

(10) Patent No.: US 8,304,204 B2
(45) Date of Patent: Nov. 6, 2012

(54) METHOD FOR MEASURING LOW-DENSITY LIPOPROTEIN (LDL) CHOLESTEROL

(75) Inventors: Takehiro Yamaguchi, Kyoto (JP); Yuka Miyake, Kyoto (JP)

(73) Assignee: Arkray, Inc., Kyoto (JP)

( * ) Notice: Subject to any disclaimer, the term of this patent is extended or adjusted under 35 U.S.C. 154(b) by 221 days.

(21) Appl. No.: 12/529,487

(22) PCT Filed: Sep. 1, 2008

(86) PCT No.: PCT/JP2008/065697
§ 371 (c)(1),
(2), (4) Date: Sep. 1, 2009

(87) PCT Pub. No.: WO2009/031506
PCT Pub. Date: Mar. 12, 2009

(65) Prior Publication Data
US 2010/0099125 A1 Apr. 22, 2010

(30) Foreign Application Priority Data
Sep. 5, 2007 (JP) ................. 2007-230253

(51) Int. Cl.
*C12Q 1/60* (2006.01)
(52) U.S. Cl. ........................................................ 435/11
(58) Field of Classification Search ................. 435/11
See application file for complete search history.

(56) References Cited

U.S. PATENT DOCUMENTS

| | | | |
|---|---|---|---|
| 5,736,406 A | 4/1998 | Miyauchi et al. | |
| 5,888,827 A | 3/1999 | Kayahara et al. | |
| 5,925,534 A | 7/1999 | Miki et al. | |
| 6,057,118 A | 5/2000 | Nakamura et al. | |
| 6,194,164 B1 * | 2/2001 | Matsui et al. | 435/11 |
| 6,333,166 B1 | 12/2001 | Nakamura et al. | |
| 6,383,819 B1 | 5/2002 | Watanabe et al. | |
| 6,762,062 B2 | 7/2004 | Watanabe et al. | |
| 6,764,828 B2 | 7/2004 | Nakamura et al. | |
| 6,939,682 B2 | 9/2005 | Tamura et al. | |
| 7,575,884 B2 * | 8/2009 | Tamura et al. | 435/11 |
| 2004/0126830 A1 | 7/2004 | Shull et al. | |
| 2004/0219623 A1 | 11/2004 | Nakamura et al. | |
| 2005/0250165 A1 | 11/2005 | Tamura et al. | |
| 2006/0008914 A1 | 1/2006 | Scheuringer | |
| 2006/0183179 A1 | 8/2006 | Nakamura et al. | |
| 2008/0131911 A1 | 6/2008 | Nakamura et al. | |
| 2011/0091917 A1 * | 4/2011 | Yamamoto et al. | 435/11 |

FOREIGN PATENT DOCUMENTS

| | | |
|---|---|---|
| CN | 1318107 A | 10/2001 |
| EP | 0990904 | 4/2000 |
| EP | 1029928 | 8/2000 |
| EP | 1114870 | 7/2001 |
| EP | 1434054 | 6/2004 |
| JP | 7-301636 | 11/1995 |
| JP | 3058602 | 7/2000 |
| JP | 2000-214170 | 8/2000 |
| JP | 3091230 | 9/2000 |
| JP | 3193634 | 7/2001 |
| JP | 2002-142799 | 5/2002 |
| JP | 3767232 | 4/2006 |
| JP | 3822340 | 9/2006 |
| WO | 02/36111 A1 | 5/2002 |
| WO | 2004/025265 | 3/2004 |
| WO | 2005/028662 | 3/2005 |

OTHER PUBLICATIONS

Extended European Search Report for European Application No. 08829199.2 dated Dec. 15, 2010.
Office Action issued in corresponding Chinese Patent Application No. 200880011758.8 dated Feb. 29, 2012.

* cited by examiner

*Primary Examiner* — Ralph Gitomer
(74) *Attorney, Agent, or Firm* — Morgan, Lewis & Bockius LLP

(57) ABSTRACT

A method for measuring LDL cholesterol in a sample using a test piece is provided which involves a step of measuring the total cholesterol in the sample; a step of measuring the non-LDL cholesterol in the sample; and a step of subtracting the non-LDL cholesterol value from the total-cholesterol value to obtain the LDL cholesterol level.

8 Claims, 7 Drawing Sheets

METHOD FOR MEASURING LOW-DENSITY LIPOPROTEIN (LDL) CHOLESTEROL

This application is a 371 national phase filing based on PCT/JP2008/065697, filed Sep. 1, 2008, which claims priority to Japanese Application No. 2007-230253, filed Sep. 5, 2007, all of which are hereby incorporated by reference in their entirety.

TECHNICAL FIELD

The present invention relates to a method for measuring low-density lipoprotein (LDL) cholesterol and a test piece for measuring LDL cholesterol.

BACKGROUND ART

LDLs are a type of lipoprotein that transports cholesterol. It has been elucidated medically that LDL cholesterol, which is a complex of an LDL and cholesterol, is one of the causative substances of arteriosclerosis. The measurement of LDL cholesterol levels newly was added in April, 2008, as a test item for medical examinations according to the Japanese Industrial Safety and Health Act.

An example of a method for measuring LDL cholesterol is to separate LDLs from other lipoproteins (e.g., high-density lipoproteins (HDLs), very low-density lipoproteins (VLDLs), etc.) by ultracentrifugation and then measure only the LDL cholesterol using an enzyme. Another example is a method in which LDLs are separated by electrophoresis, lipids then are stained and the extent of color development thereof is measured. Although these methods are generally-used measurement methods, their operation is troublesome and it is difficult to process a large number of specimens. Therefore, these methods are not applicable to clinical examinations or the like.

Thus, a variety of methods for measuring LDL cholesterol for use in a liquid system in which an enzyme reagent is used have been developed, and some are in use. Since such measurement methods that use an enzyme reagent can be performed using an autoanalyzer, they are of use in clinical examinations where a large number of specimens need to be processed. Examples of such measurement methods that use an enzyme reagent include a direct method in which LDL cholesterol itself is directly measured, an elimination method in which types of cholesterol other than LDL cholesterol (non-LDL cholesterol) are subjected to a reaction and eliminated in a first reaction and the remaining LDL cholesterol is subjected to a reaction in a second reaction to measure an LDL cholesterol level, and like methods.

An example of the direct method is a method in which a direct measurement of LDL cholesterol is performed using an enzyme reagent whose specificity to LDL cholesterol is enhanced by cyclodextrin and a surfactant (Patent Document 1). Examples of the elimination method include methods in which a reaction between LDL cholesterol and an enzyme reagent is inhibited, or the reactivity of an enzyme reagent with non-LDL cholesterol is enhanced, using a polyanion and a divalent metal ion (Patent Document 2), a polyanion (Patent Document 3), calixarene sulfate (Patent Document 4) or amine (Patent Document 5). Liquid-system reagents for use in the direct method and the elimination method are available from different manufacturers.

Patent Document 1: JP 3091230B
Patent Document 2: JP 3193634B
Patent Document 3: JP 3767232B
Patent Document 4: JP 3822340B
Patent Document 5: JP 3058602B

DISCLOSURE OF INVENTION

However, conventional measurement methods require large-scale autoanalyzers. Large-scale autoanalyzers need large installation spaces and are costly. Therefore, while such measurement devices can be introduced into large-scale hospitals, their introduction into ordinary clinics is difficult. Furthermore, conventional measurement methods are not applicable to test pieces that retain a reagent in a dry state (dry system), and their use is limited to a liquid system only. Liquid-system measurements require large amounts of rinsing water and generate liquid waste due to rinsing.

An object of the present invention is thus to provide a method for measuring LDL cholesterol that allows a small measurement device of a simple configuration to measure LDL cholesterol and that can be applicable to a test piece, and a test piece for measuring LDL cholesterol for use with the method.

In order to accomplish the object stated above, the measurement method of the present invention is a low-density lipoprotein (LDL) cholesterol measurement method for measuring LDL cholesterol in a sample and has steps (A) to (D) as follows:

(A) a step of providing a total-cholesterol measurement portion and a non-LDL cholesterol measurement portion for measuring non-LDL cholesterol, which is cholesterol other than LDL cholesterol, (B) a step of measuring the total cholesterol in the sample in the total-cholesterol measurement portion, (C) a step of measuring non-LDL cholesterol in the sample in the non-LDL cholesterol measurement portion, and (D) a step of obtaining the LDL cholesterol level in the sample by subtracting the non-LDL cholesterol value measured in the step (C) from the total-cholesterol value measured in the step (B).

The test piece of the present invention is a test piece for measuring low-density lipoprotein (LDL) cholesterol for use with the method for measuring LDL cholesterol of the present invention, and the test piece comprises:

a total-cholesterol measurement portion, and a non-LDL cholesterol measurement portion for measuring a non-LDL cholesterol level, which is the level of cholesterol other than LDL cholesterol, and an LDL cholesterol level is obtained by subtracting the non-LDL cholesterol value measured in the non-LDL cholesterol measurement portion from the total-cholesterol value measured in the total-cholesterol measurement portion.

The inventors carried out a series of research in order to accomplish the object described above. During the course of research, measurement methods using conventional elimination methods were examined. With a liquid-system reagent for measuring LDL cholesterol (wet chemistry) using the elimination methods, non-LDL cholesterol is, as stated above, subjected to a first reaction for elimination, and the remaining LDL cholesterol is subjected to a second reaction. In other words, in this reaction system, a pretreatment step is necessary to obtain a specimen from which non-LDL cholesterol has been eliminated or a reaction liquid containing a specimen from which non-LDL cholesterol has been eliminated. It thus was found that it is not possible in principle to process a liquid-system reagent for measuring LDL cholesterol that is for use with the elimination method into a test piece without further treatment. The inventors then found as a result of their further research that a test piece can be obtained using a configuration such that the total-cholesterol measurement portion and the non-LDL cholesterol measurement portion are provided separately and independently, the total cholesterol is measured in the total-cholesterol measurement portion, the non-LDL cholesterol is measured in the non-LDL cholesterol measurement portion and an LDL cholesterol level is obtained by subtracting the measured non-LDL cholesterol value from the measured total-cholesterol value, and the inventors then arrived at the present invention. According to the present invention, the structure of a measurement device can be simple and the measurement device can be small, and it is thus possible to realize a low-cost and space saving. Therefore, the present invention enables an LDL cholesterol measurement device to be introduced into, not only, e.g., large-scale hospitals, but also ordinary clinics. Moreover, the principle of the measurement method of the present invention is readily applicable to a test piece. Furthermore, since use of the test piece of the present invention does not require rinsing water or generate liquid waste, the present invention can also contribute to the environment and to the simplification of measurements.

DESCRIPTION OF THE INVENTION

Figure 1A:
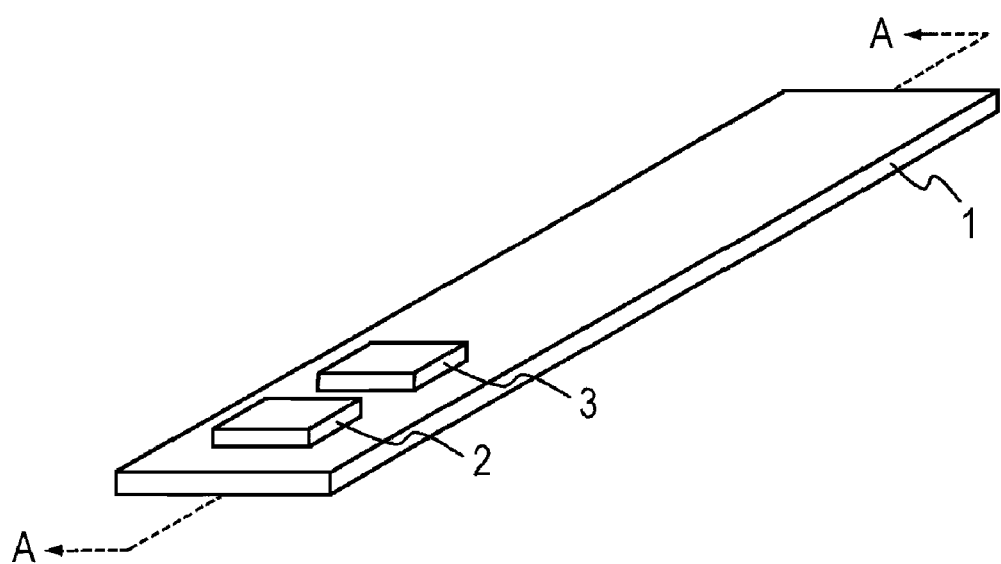
FIG. 1(A) is a perspective view of an example of the test piece of the present invention.

Although it is preferable that the measurement method of the present invention is applied to a test piece as described above, the present invention is not limited to this application and may be applied to a liquid system.

In the measurement method of the present invention, the order of the step (B) and the step (C) is not particularly limited, and either step may be performed earlier, or both steps may be performed simultaneously.

The following configuration is preferable for the measurement method of the present invention:
in the step (A), the total-cholesterol measurement portion contains an enzyme reagent for measuring cholesterol, and
  the non-LDL cholesterol measurement portion contains an enzyme reagent for measuring cholesterol, a surfactant for solubilizing non-LDL cholesterol and a surfactant for inhibiting LDL cholesterol dissolution,
in the step (B), the total cholesterol is measured by the enzyme reagent for measuring cholesterol, and
in the step (C), due to the actions of the surfactant for solubilizing non-LDL cholesterol and the surfactant for inhibiting LDL cholesterol dissolution, the non-LDL cholesterol is measured selectively by the enzyme reagent for measuring cholesterol. With conventional techniques, it is difficult to measure LDL cholesterol separately from VLDL cholesterol, but the use of this configuration allows the separate measurement, thereby enhancing the accuracy and reliability of the LDL cholesterol measurement.

It is preferable that in the measurement method of the present invention, the surfactant for solubilizing non-LDL cholesterol contains at least one surfactant selected from polyoxyethylene alkylene phenyl ethers and polyoxyethylene alkylene tribenzyl phenyl ethers; and the surfactant for inhibiting LDL cholesterol dissolution contains at least one surfactant selected from the group consisting of polyoxyethylene alkyl ethers, polyoxyethylene alkyl phenyl ethers, polyoxyethylene-polyoxypropylene condensation products, polyoxyethylene alkyl ether sulfate salts and alkylbenzene sulfonate salts.

In the measurement method of the present invention, the enzyme reagent may be in a form containing a cholesterol esterase and a cholesterol oxidase.

In the measurement method of the present invention, the enzyme reagent may be in a form containing a cholesterol esterase and a cholesterol dehydrogenase.

The following configuration is more preferable for the measurement method of the present invention: in the step (A), the non-LDL cholesterol measurement portion further contains an LDL cholesterol agglomerating agent; and in the step (C), due to the actions of the surfactant for solubilizing non-LDL cholesterol, the surfactant for inhibiting LDL cholesterol dissolution and the LDL cholesterol agglomerating agent, the non-LDL cholesterol is measured selectively with the enzyme reagent for measuring cholesterol. With conventional techniques, it is difficult to measure LDL cholesterol separately from VLDL cholesterol, but the use of this configuration allows the separate measurement, thereby further enhancing the accuracy and reliability of the LDL cholesterol measurement. The LDL cholesterol agglomerating agent is preferably a polyvinyl sulfate salt.

In the measurement method of the present invention, the non-LDL cholesterol may be high-density lipoprotein (HDL) cholesterol and very-low-density lipoprotein (VLDL) cholesterol.

For the same reason as described above, the following configuration is preferable for the test piece of the present invention:
the total-cholesterol measurement portion contains an enzyme reagent for measuring cholesterol, and
the non-LDL cholesterol measurement portion contains an enzyme reagent for measuring cholesterol, a surfactant for solubilizing non-LDL cholesterol and a surfactant for inhibiting LDL cholesterol dissolution.

In the test piece of the present invention, the enzyme reagent may be in a form containing a cholesterol esterase and a cholesterol oxidase.

In the test piece of the present invention, the enzyme reagent may be in a form containing a cholesterol esterase and a cholesterol dehydrogenase.

It is preferable that in the test piece of the present invention, the surfactant for solubilizing non-LDL cholesterol contains at least one surfactant selected from polyoxyethylene alkylene phenyl ethers and polyoxyethylene alkylene tribenzyl phenyl ethers, and the surfactant for inhibiting LDL cholesterol dissolution contains at least one surfactant selected from the group consisting of polyoxyethylene alkyl ethers, polyoxyethylene alkyl phenyl ethers, polyoxyethylene-polyoxypropylene condensation products, polyoxyethylene alkyl ether sulfate salts and alkylbenzene sulfonate salts.

For the same reason as described above, a preferable configuration of the test piece of the present invention is such that the non-LDL cholesterol measurement portion further contains an LDL cholesterol agglomerating agent. The LDL cholesterol agglomerating agent is preferably a polyvinyl sulfate salt.

In the test piece of the present invention, the non-LDL cholesterol may be high-density lipoprotein (HDL) cholesterol and very-low-density lipoprotein (VLDL) cholesterol.

The test piece of the present invention may be in a form including a support, a first reagent layer and a second reagent layer, wherein
the first reagent layer and the second reagent layer are disposed on the support,
the first reagent layer serves as the total-cholesterol measurement portion, and
the second reagent layer serves as the non-LDL cholesterol measurement portion.

The test piece of the present invention may be in a form including a first support, a second support, a first reagent layer and a second reagent layer, wherein
the first reagent layer is disposed on the first support,
the second reagent layer is disposed on the second support,
the first reagent layer serves as the total-cholesterol measurement portion, and
the second reagent layer serves as the non-LDL cholesterol measurement portion.

Next, the present invention is described in detail with reference to examples. In the present invention, "the ratio relative to the total components upon sample application" means the ratio relative to the total components upon application of a sample (specimen) to the total-cholesterol measurement portion (for example, the first reagent layer) or the non-LDL cholesterol measurement portion (for example, the second reagent layer), and "the total components" refers to all the components that are present upon the sample application, such as the sample, enzyme reagent for measuring cholesterol, surfactant for solubilizing non-LDL cholesterol, surfactant for inhibiting LDL cholesterol dissolution, LDL cholesterol agglomerating agent, etc. Usually, the amount of one specimen can be predicted or determined based on its type.

The test piece of the present invention may be configured, for example, such that the total-cholesterol measurement portion and the non-LDL cholesterol measurement portion are disposed on one support.

Moreover, the test piece of the present invention may be configured such that the total-cholesterol measurement portion is disposed on a first support and the non-LDL cholesterol measurement portion is disposed on a second support.

In the test piece of the present invention, the total-cholesterol measurement portion can be configured, for example, such that a first reagent layer (reagent portion) is formed on a support and the first reagent layer contains an enzyme reagent for measuring cholesterol. It is preferable that the first reagent layer further contains a surfactant for solubilizing cholesterol. The first reagent layer may be configured to include a reaction layer and a detection layer wherein the reaction layer contains the surfactant for solubilizing cholesterol and the detection layer contains the enzyme reagent for measuring cholesterol. Moreover, another preferable configuration is such that the reaction layer contains part of the enzyme reagent for measuring cholesterol and the surfactant for solubilizing cholesterol, and the detection layer contains the rest of the enzyme reagent for measuring cholesterol.

In the test piece of the present invention, the non-LDL cholesterol measurement portion can be configured, for example, such that a second reagent layer (reagent portion) is formed on a support, and the second reagent layer contains an enzyme reagent for measuring cholesterol, the surfactant for solubilizing non-LDL cholesterol and the surfactant for inhibiting LDL cholesterol dissolution. The second reagent layer may be configured to include a reaction layer and a detection layer wherein the reaction layer contains the surfactant for solubilizing non-LDL cholesterol and the surfactant for inhibiting LDL cholesterol dissolution and the detection layer contains the enzyme reagent for measuring cholesterol. Furthermore, a preferable configuration is such that, within the reaction layer, the upper part thereof (upper layer) contains the surfactant for inhibiting LDL cholesterol dissolution and the lower part thereof (lower layer) contains the surfactant for solubilizing non-cholesterol. Moreover, another preferable configuration is such that the reaction layer contains part of the enzyme reagent for measuring cholesterol, the surfactant for solubilizing non-LDL cholesterol and the surfactant for inhibiting LDL cholesterol dissolution, and the detection layer contains the rest of the enzyme reagent for measuring cholesterol.

It is preferable that the second reagent layer further contains the LDL cholesterol agglomerating agent. The second reagent layer may be configured to include a reaction layer and a detection layer wherein the reaction layer contains the surfactant for solubilizing non-LDL cholesterol, the surfactant for inhibiting LDL cholesterol dissolution and the LDL cholesterol agglomerating agent and the detection layer contains the enzyme reagent for measuring cholesterol. Furthermore, a more preferable configuration is such that, within the reaction layer, the upper part thereof (upper layer) contains the surfactant for inhibiting LDL cholesterol dissolution and the LDL cholesterol agglomerating agent, and the lower part thereof (lower layer) contains the surfactant for solubilizing non-LDL cholesterol. Moreover, a more preferable configuration is such that the reaction layer contains part of the enzyme reagent for measuring cholesterol, the surfactant for solubilizing non-LDL cholesterol, the surfactant for inhibiting LDL cholesterol dissolution and the LDL cholesterol agglomerating agent, and the detection layer contains the rest of the enzyme reagent for measuring cholesterol.

In the present invention, the surfactant for solubilizing non-LDL cholesterol is not particularly limited as long as it has an ability to solubilize non-LDL cholesterol (such as HDL cholesterol, VLDL cholesterol, etc.) more than LDL cholesterol. The surfactant for solubilizing non-LDL cholesterol has a function of solubilizing cholesterol or cholesterol esters contained in non low-density lipoproteins, and as a result, will promote the reaction between the cholesterol or esters thereof and the enzyme reagent. As described above, the surfactant for solubilizing non-LDL cholesterol preferably includes a polyoxyethylene alkylene phenyl ether and a polyoxyethylene alkylene tribenzyl phenyl ether, and these may be used singly or in combination. The more preferable of these is a polyoxyethylene alkylene tribenzyl phenyl ether. Examples of commercially available products of polyoxyethylene alkylene phenyl ethers include "Emulgen A-60" (trade name, manufactured by Kao Corporation), "Nonipol 40" (trade name, manufactured by a Sanyo Chemical Industries, Ltd.), etc., and examples of commercially available products of polyoxyethylene alkylene tribenzyl phenyl ethers include "Emulgen B66" (trade name, manufactured by Kao Corporation), "Blaunon TBP-15-95" (trade name, manufactured by Aoki Oil Industrial Co., Ltd.), etc.

In the present invention, the surfactant for solubilizing cholesterol for use in the total-cholesterol measurement portion is not particularly limited as long as it can solubilize all lipoproteins, and, for example, sodium deoxycholate and polyoxyethylene (n)octylphenyl ether (for example, "Triton X-100" (trade name, manufactured by Wako Pure Chemical Industries, Ltd.)) can be used.

In the present invention, the surfactant for inhibiting LDL cholesterol dissolution is not particularly limited as long as it inhibits the dissolution of LDL cholesterol. The inhibition of the dissolution of LDL cholesterol by the surfactant for inhibiting LDL cholesterol dissolution will inhibit the reaction between the LDL cholesterol or esters thereof and the enzyme reagent. As described above, preferable examples of the surfactant for inhibiting LDL cholesterol dissolution include polyoxyethylene alkyl ethers, polyoxyethylene alkyl phenyl ethers, polyoxyethylene-polyoxypropylene condensation products, polyoxyethylene alkyl ether sulfate salts and alkylbenzene sulfonate salts, which may be used singly or as a combination of two or more. Particularly preferable among these are polyoxyethylene-polyoxypropylene condensation products. A preferable polyoxyethylene alkyl ether is polyoxyethylene cetyl ether (for example, "Emulgen 220" (trade name, manufactured by Kao Corporation)). A preferable polyoxyethylene alkyl phenyl ether is polyoxyethylene nonylphenyl ether (for example, "Blaunon N-502" (trade name, manufactured by Aoki Oil Industrial Co., Ltd.). A preferable polyoxyethylene-polyoxypropylene condensation product is "Pluronic F-88" (trade name, manufactured by ADEKA Corporation). A preferable polyoxyethylene alkyl ether sulfate salt is sodium polyoxyethylene lauryl ether sulfate (for example, "Emal 20C" (trade name, manufactured by Kao Corporation)). A preferable alkylbenzene sulfonate salt is sodium dodecylbenzene sulfonate. These can be used singly or in a combination of two or more.

In the total-cholesterol measurement portion (for example, the first reagent layer) in the test piece of the present invention, the ratio of the surfactant for solubilizing cholesterol relative to the total components upon sample application is, for example, in a range of 0.05 to 3.0 wt %, preferably in a range of 0.1 to 1.0 wt % and more preferably in a range of 0.3 to 0.7 wt %.

In the non-LDL cholesterol measurement portion (for example, the second reagent layer) in the test piece of the present invention, the ratio of the surfactant for solubilizing non-LDL cholesterol relative to the total components upon sample application is, for example, in a range of 1 to 15 wt %, preferably in a range of 2 to 10 wt % and more preferably in a range of 4 to 8 wt %. Moreover, the ratio of the surfactant for inhibiting LDL cholesterol dissolution relative to the total components upon sample application is, for example, in a range of 1 to 15 wt %, preferably in a range of 1.5 to 10 wt % and more preferably in a range of 2 to 6 wt %. The weight ratio (A/B) of the surfactant for solubilizing non-LDL cholesterol (A) and the surfactant for inhibiting LDL cholesterol dissolution (B) is, for example, in a range of 1/1 to 4/1, preferably in a range of 1.1/1 to 3/1 and more preferably in a range of 1.2/1 to 2.5/1.

In the present invention, the LDL cholesterol agglomerating agent is not particularly limited, and examples include polyvinyl sulfate salts, water-soluble anionic polymers, plant-derived lectin, polyethylene glycol (PEG), phosphotungstic acid, dextran sulfate, dextran sulfate salts, heparin and the like, and polyvinyl sulfate salts are preferable as described above.

Examples of the polyvinyl sulfate salts include potassium polyvinyl sulfate, sodium polyvinyl sulfate, lithium polyvinyl sulfate, ammonium polyvinyl sulfate, etc., and these may be used singly or in a combination of two or more. More preferable among these is potassium polyvinyl sulfate. Among the polyvinyl sulfate salts, those that have 70% of the sulfuric acid groups in side chains are preferable. Moreover, the degree of esterification of the polyvinyl sulfate salts is preferably 80% or greater and more preferably 90% or greater. Furthermore, addition of polyglycol methyl ether or polyvinyl pyrrolidone to the polyvinyl sulfate salts further enhances the agglomeration reaction of LDL and is thus preferable.

The water-soluble anionic polymers are not particularly limited and examples include homopolymers made from monomers such as acrylic acid (2-phospho-1,1-dimethylethylamide), 2-acrylamide glycolic acid, 2-acrylamide-2-methyl-1-propanesulfonic acid and 2-acrylamide-2-methyl-1-propanesulfonic acid-CO-2-acrylamide glycolic acid, copolymers made from these monomers, poly(meth)acrylate ester, etc. Specific examples of the water-soluble anionic polymers include polyacrylic acid-(2-phospho-1,1-dimethylethylamide) (PAP), poly-2-acrylamide glycolic acid (PAAG), poly-(2-acrylamide-2-methyl-1-propanesulfonic acid) (PAMPS), poly-(2-acrylamide-2-methyl-1-propanesulfonic acid-CO-2-acrylamide glycolic acid) [P(AMPS-AAG)], etc.

The plant-derived lectin is not particularly limited and examples include lectin derived from seeds of castor (*Ricinus communis*), soybeans, etc.

The polyethylene glycol (PEG), phosphotungstic acid, dextran sulfate and heparin may be used singly or in combination with, for example, cations such as a magnesium ion, a manganese ion, a calcium ion, a lithium ion and a nickel ion.

In the test piece of the present invention, the ratio of the LDL cholesterol agglomerating agent relative to the total components upon sample application is, for example, in a range of 0.01 to 0.30 wt %, preferably in a range of 0.02 to 0.20 wt % and more preferably in a range of 0.04 to 0.15 wt %. In the test piece of the present invention, the ratio of the polyglycol methyl ether relative to the total components upon sample application is, for example, in a range of 3 to 12 wt %, preferably in a range of 3.5 to 11 wt % and more preferably in a range of 4 to 10 wt %.

As described above, a combination of a cholesterol esterase and a cholesterol oxidase or a combination of a cholesterol esterase and a cholesterol dehydrogenase is preferable as the enzyme reagent for measuring cholesterol. The former combination is the more preferable.

In the test piece of the present invention, the ratio of cholesterol esterase relative to the total components upon sample application is, for example, in a range of 5 to 1000 U/mL, preferably in a range of 10 to 100 U/mL and more preferably in a range of 30 to 70 U/mL. In the test piece of the present invention, the ratio of cholesterol oxidase relative to the total components upon sample application is, for example, in a range of 5 to 1000 U/mL, preferably in a range of 10 to 100 U/mL, and more preferably in a range of 20 to 50 U/mL. In the test piece of the present invention, the ratio of cholesterol dehydrogenase relative to the total components upon sample application is, for example, in a range of 5 to 1000 U/mL, preferably in a range of 10 to 100 U/mL, and more preferably in a range of 30 to 70 U/mL.

Commercial products, for example, can be used as the enzyme reagent for measuring cholesterol, and purified products that do not contain impurities that inhibit the series of reactions as well as genetically modified products and the like preferably can be used.

The cholesterol esterase is not particularly limited, and examples include enzymes derived from microorganisms belonging to, for example, *Pseudomonas* and *Trichoderma*. These enzymes are not particularly limited and examples include those that have substrate specificity as shown in the table below. Moreover, for example, BSA or the like may be added to these enzymes, and there is no particular limitation.

Substrate Specificity of Enzyme

| Substrate | Range of Specific Activity (%) |
| --- | --- |
| Cholesterol Acetate | 0.1-50 |
| Cholesterol Propionate | 0-50 |
| Cholesterol Butyrate | 1-50 |
| Cholesterol Palmitate | 1-200 |
| Cholesterol Stearate | 0-50 |
| Cholesterol Oleate | 1-200 |
| Cholesterol Linolate | 100 |
| Cholesterol Caprinate | 0-100 |
| Cholesterol Laurinate | 0-200 |
| Cholesterol Myristate | 0-200 |

Normally, cholesterol in a living body is classified into two types, i.e., a free state and a state that forms an ester bond with a fatty acid. Therefore, cholesterol in the latter state is hydrolyzed by a cholesterol esterase into cholesterol and a fatty acid. When the resulting cholesterol and the former free cholesterol are treated with a cholesterol oxidase, cholestenone and hydrogen peroxide are produced. A cholesterol level can be obtained by measuring this hydrogen peroxide. Although the measurement of hydrogen peroxide is performed electrochemically or chemically, a chemical measurement that uses peroxidase (POD) and a substrate that develops a color upon oxidation (hereinafter referred to as an "oxidatively chromogenic substrate") is preferable. In this case, POD and the oxidatively chromogenic substrate will be contained in the enzyme reagent for measuring cholesterol. In the test piece of the present invention, the ratio of POD relative to the total components upon sample application is, for example, in a range of 50 to 5000 U/mL, preferably in a range of 100 to 1500 U/mL, and more preferably in a range of 700 to 800 U/mL. In the test piece of the present invention, the ratio of the oxidatively chromogenic substrate relative to the total components upon sample application is determined suitably according to its type, but it is in a range of, for example, 10 to 1000 mmol/L, preferably in a range of 20 to 200 mmol/L, and more preferably in a range of 30 to 70 mmol/L.

Examples of the oxidatively chromogenic substrate include ALPS [N-ethyl-N-(3-sulfopropyl)aniline, sodium salt], DAOS [N-ethyl-N-(2-hydroxy-3-sulfopropyl)-3,5-dimethoxyaniline, sodium salt], MAOS [N-ethyl-N-(2-hydroxy-3-sulfopropyl)-3,5-dimethylaniline, sodium salt, monohydrate], TOOS [N-ethyl-N-(2-hydroxy-3-sulfopropyl)-3-methylaniline, sodium salt, dihydrate], phenol and the like, and a substrate that gives a color that matches the wavelength used by a measurement device can be selected suitably among these examples.

In the test piece of the present invention, it is preferable that the total-cholesterol measurement portion and the non-LDL cholesterol measurement portion are adjusted such that the pH thereof upon sample application is in a range of pH 6 to 9. A preferable pH range is 7 to 8, and optimally, the pH of the total-cholesterol measurement portion is 7.5, and the pH of the non-LDL cholesterol measurement portion is 7.7. For adjustment to the pH range, the total-cholesterol measurement portion (for example, the first reagent layer) and the non-LDL cholesterol measurement portion (for example, the second reagent layer) preferably contain a buffer. Examples of the buffer include those that will be described below.

Samples that are the objects of measurement are not particularly limited, and examples are samples of specimens (biological fluid, in particular) that may contain LDL cholesterol, such as whole blood, plasma, serum, and the like.

Figure 1B:
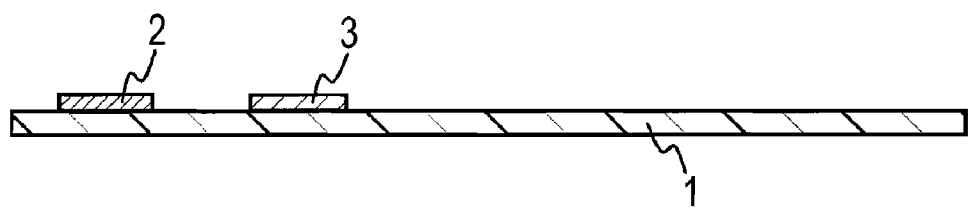
FIG. 1(B) is a cross-sectional view when viewed in the direction indicated by A-A in FIG. 1(A).

Next, an example of the test piece of the present invention is shown in FIG. 1. FIG. 1(A) is a perspective view of the test piece of this example, and FIG. 1(B) is a cross-sectional view obtained when viewed in the direction of A-A of FIG. 1(A). The test piece of this example is configured such that two reagent layers (reagent layer 2 and reagent layer 3) are disposed at one end of a long and narrow, rectangular, plate-like support 1. Of the two reagent layers 2 and 3, one serves as the total-cholesterol measurement portion (first reagent layer) and the other serves as the non-LDL cholesterol measurement portion (second reagent layer).

The support 1 can be produced using a resin such as polyethylene terephthalate (PET), polystyrene, polyester or cellulose acetate, and of these resins PET is preferable. The thickness of the support 1 is not particularly limited and is in a range of, for example, 0.1 to 1 mm, preferably in a range of 0.1 to 0.5 mm and more preferably in a range of 0.2 to 0.3 mm.

For example, the enzyme reagent for measuring cholesterol, the surfactant for solubilizing non-LDL cholesterol, the surfactant for inhibiting LDL cholesterol dissolution, etc., are contained in the reagent layer (reagent portion) that serves as the non-LDL cholesterol measurement portion, and the LDL cholesterol agglomerating agent is preferably further contained. For example, the enzyme reagent for measuring cholesterol, the surfactant for solubilizing cholesterol, etc., are contained in the reagent layer that serves as the total-cholesterol measurement portion.

The reagent layers 2 and 3 can be produced by impregnating a fibrous structure or the like with or applying thereto a solution prepared by dissolving and mixing in a solvent a hydrophilic polymer and various reagents, such as the enzyme reagent for measuring cholesterol, the various surfactants, and the LDL cholesterol agglomerating agent, followed by drying.

Examples of the hydrophilic polymer include polyvinyl pyrrolidone, hydroxypropylcellulose, methylcellulose, sodium alginate, polyacrylic acid, gelatin, acid-hydrolyzed gelatin, polyacrylamide, agarose, etc.

Examples of the solvent include phosphate buffers, Good's buffers, Tris-HCl buffers, etc. A phosphate buffer is preferable as the solvent for use in the total-cholesterol measurement portion, and a Good's buffer is preferable as the solvent for use in the non-LDL cholesterol measurement portion. Preferable examples of Good's buffers are PIPES, TES, HEPES, DIPSO, TAPSO, MES, etc., and TES is particularly preferable. It is preferable that the pH of the buffers is adjusted to be in a range of 6 to 9 and more preferably in a range of 7 to 8 so that the pH upon sample application will be within the aforementioned specific range, and optimally the pH of the total-cholesterol measurement portion is adjusted to 7.5 and the pH of the non-LDL cholesterol measurement portion is adjusted to 7.7. The ratio of the hydrophilic polymer is in a range of, for example, 0 to 40 wt % and more preferably 10 to 30 wt % of the total amount of the solution to be applied, and can be suitably adjusted according to its type. The enzyme reagent for measuring cholesterol, the various surfactants and the LDL cholesterol agglomerating agent are adjusted in advance such that they will be contained in the solution in the ratios specified above.

The fibrous structure is not particularly limited. The fiber may be of a kind of material that does not inhibit the measurement, and may be structured into a knitted or nonwoven fabric. Examples of the fiber include fibers made of rayon, nylon, polyester and like, including a composite of these fibers.

The methods of the application of the solution are not particularly limited, and examples include a method in which a brush or the like is used, a spray coating method, a method in which a roll coater is used, a dipping method, and the like.

The thicknesses of the reagent layers 2 and 3 are each in a range of, for example, 50 to 250 µm, preferably in a range of 80 to 200 µm and more preferably in a range of 100 to 150 µm. The thicknesses of the reagent layers 2 and 3 are not the thicknesses after the application and drying of the solution, but are the thicknesses immediately after the application of the solution. The reagent layers 2 and 3 may contain, in addition to the aforementioned components, additives such as antioxidants as necessary. The test piece of this example can be prepared by affixing the reagent layers 2 and 3 to specific locations of the support 1. In the present invention, the shape of the test piece is not particularly limited, and is in the form of, for example, a plate or a strip. When the test piece is in the form of a strip, the size thereof is in a range of, for example, 50 to 150 mm for the overall length and in a range of 3 to 15 mm for the width, and preferably in a range of 60 to 100 mm for the overall length and in a range of 5 to 10 mm for the width.

The test piece of this example is used, for example, in the following manner. Below, the reagent layer 2 is a non-LDL cholesterol measurement portion, and the reagent layer 3 is a total-cholesterol measurement portion. That is, first, a specimen such as blood is dripped from above the reagent layer 2 and the reagent layer 3. Of the specimen dripped over the reagent layer 2, only the non-LDL cholesterol reacts with the enzyme reagent for measuring cholesterol due to the actions of the surfactant for solubilizing non-LDL cholesterol and the surfactant for inhibiting LDL cholesterol dissolution contained in the reagent layer 2. If the reagent layer 2 further contains the LDL cholesterol agglomerating agent, the function of the LDL cholesterol agglomerating agent is exerted and only the non-LDL cholesterol reacts with the enzyme reagent for measuring cholesterol more effectively. On the other hand, with regard to the reagent layer 3, the entirety of the cholesterol in the dripped specimen reacts with the enzyme reagent for measuring cholesterol due to the action of the surfactant for solubilizing cholesterol contained in the reagent layer. When the reagent layer 2 and the reagent layer 3 contain POD and the oxidatively chromogenic substrate, color development of the substrate is measured with an optical measuring instrument such as a spectrophotometer or a reflectometer. When color development of a plasma or serum sample is measured, if the support 1 transmits light, the test piece may be irradiated on the support 1 side or on the reagent layer (reagent layers 2 and 3) side, and the transmittance, reflectivity or the like in connection with the irradiation then is measured. If the support 1 does not transmit light, the test piece is irradiated on the reagent layer (reagent layers 2 and 3) side, and reflectivity then is measured. When a sample is whole blood as described below, it is preferable to provide a blood-cell shielding layer and a light reflection layer between the detection layer and the reaction layer to prevent the color of red blood cells from interfering with the measurement of light, to use a light-transmitting support, and to carry out a measurement on this support 1 side.

Figure 2:
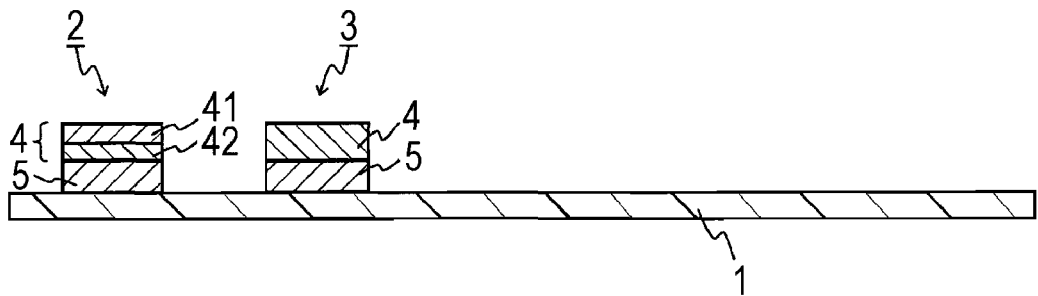
FIG. 2 is a cross-sectional view of another example of the test piece of the present invention.

FIG. 2 shows a cross-sectional view of another example of the test piece of the present invention. In the test piece of this example, a reagent layer 2 that serves as the non-LDL cholesterol measurement portion and a reagent layer 3 that serves as the total-cholesterol measurement portion are formed on a support 1, and the reagent layers 2 and 3 are both provided with a reaction layer 4 and a detection layer 5 as shown in the figure. Otherwise, the test piece is identical to the test piece shown in FIG. 1 above and is used in the same manner. In the reagent layer 2, the reaction layer 4 contains the surfactant for solubilizing non-LDL cholesterol, the surfactant for inhibiting LDL dissolution and the LDL cholesterol agglomerating agent; and the reaction layer 5 contains the enzyme reagent for measuring cholesterol. In the reagent layer 3, the reaction layer 4 contains the surfactant for solubilizing cholesterol, and the detection layer 5 contains the enzyme reagent for measuring cholesterol.

Furthermore, in the reagent layer 2, the reaction layer 4 may be divided into an upper layer 41 and a lower layer 42, and the upper layer 41 may contain the surfactant for inhibiting LDL cholesterol dissolution and the LDL cholesterol agglomerating agent and the lower layer 42 may contain the surfactant for solubilizing non-LDL cholesterol. With this configuration, first, a sample comes into contact with the surfactant for inhibiting LDL cholesterol dissolution and the LDL cholesterol agglomerating agent in the upper layer 41, and the sample then moves into the lower layer 42 and comes into contact with the surfactant for solubilizing non-LDL cholesterol and subsequently the enzyme reagent in the detection layer 5. In this manner, by dividing the reaction layer into two layers, i.e., an upper layer and a lower layer, according to the movement of a sample, the dissolution of LDL cholesterol can be prevented more effectively, thereby enhancing the accuracy of the measurement of non-LDL cholesterol. The reaction layer 4 of this configuration can be formed, for example, in the following manner: a solution of the enzyme reagent for measuring cholesterol is applied to a fibrous structure and dried to form the detection layer 5; a solution in which the surfactant for solubilizing non-LDL cholesterol and the hydrophilic polymer are dissolved in a solvent is applied thereto and dried; and a solution in which the surfactant for inhibiting LDL cholesterol dissolution, the LDL cholesterol agglomerating agent and the hydrophilic polymer are dissolved in a solvent is applied thereto and dried. The type, concentration and like factors of the hydrophilic polymer and the solvents in the present case are the same as above, and the method of application of the solutions is also the same as above. The reagent layer 3 having a two-layer structure can be formed according to the method of forming the reagent layer 2 described above in which the solutions are applied one over the other. In addition to the method of forming a reagent layer of a multilayer structure by applying one solution over another, a reagent layer of a multilayer structure can be formed also by applying reagent solutions to different fibrous structures followed by drying and then laminating the structures.

Figure 3:
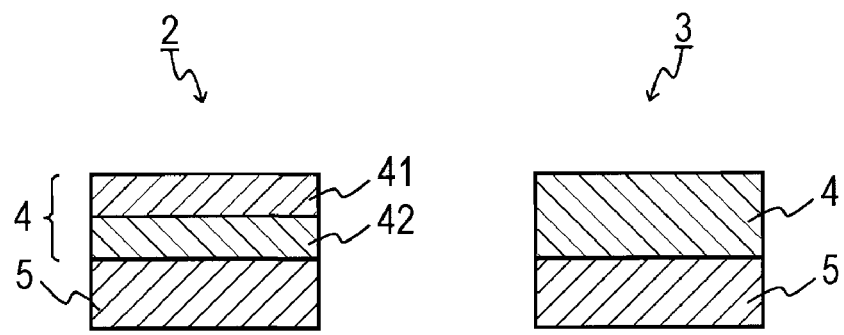
FIG. 3 is a cross-sectional view of still another example of the test piece of the present invention.

FIG. 3 is a cross-sectional view of still another example of the test piece of the present invention. In the test piece of this example, there is no support, and a reagent layer 2 that serves as the non-LDL cholesterol measurement portion and a reagent layer 3 that serves as the total-cholesterol measurement portion are each formed as separate test piece units. The reagent layers 2 and 3 are both provided with a reaction layer 4 and a detection layer 5 as shown in the figure. As described above, in the reagent layer 2, the reaction layer 4 may be divided into an upper layer 41 and a lower layer 42, and the upper layer 41 may contain the surfactant for inhibiting LDL cholesterol dissolution and the LDL cholesterol agglomerating agent and the lower layer 42 may contain the surfactant for solubilizing non-LDL cholesterol. Otherwise, the test piece is identical to the test piece shown in FIG. 1 above and is used in the same manner. In the reagent layer 2, the reaction layer 4 contains the surfactant for solubilizing non-LDL cholesterol, the surfactant for inhibiting LDL dissolution and the LDL cholesterol agglomerating agent; and the reaction layer 5 contains the enzyme reagent for measuring cholesterol. In the reagent layer 3, the reaction layer 4 contains the surfactant for solubilizing cholesterol, and the detection layer 5 contains the enzyme reagent for measuring cholesterol.

Figure 4:
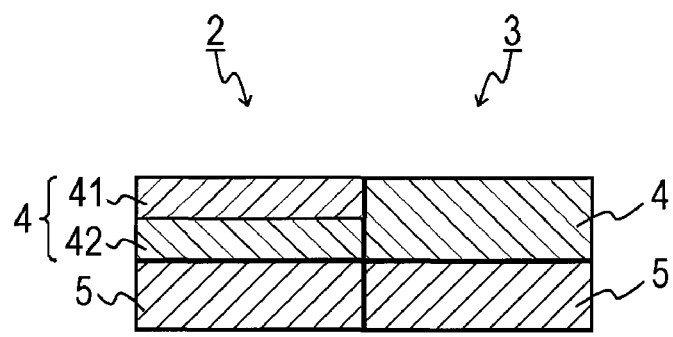
FIG. 4 is a cross-sectional view of still another example of the test piece of the present invention.

FIG. 4 is a cross-sectional view of still another example of the test piece of the present invention. In the test piece of this example, the test piece is divided perpendicularly in half relative to the surface to which a sample is applied, and one half is for use as a reagent layer 2 that serves as the non-LDL cholesterol measurement portion and the other half is for use as a reagent layer 3 that serves as the total-cholesterol measurement portion. The reagent layers 2 and 3 are both provided with a reaction layer 4 and a detection layer 5 as shown in the figure. As described above, in the reagent layer 2, the reaction layer 4 may be divided into an upper layer 41 and a lower layer 42, and the upper layer 41 may contain the surfactant for inhibiting LDL cholesterol dissolution and the LDL cholesterol agglomerating agent and the lower layer 42 may contain the surfactant for solubilizing non-LDL cholesterol. Otherwise, the test piece is identical to the test piece shown in FIG. 1 above and is used in the same manner. In the reagent layer 2, the reaction layer 4 contains the surfactant for solubilizing non-LDL cholesterol, the surfactant for inhibiting LDL dissolution and the LDL cholesterol agglomerating agent, and the reaction layer 5 contains the enzyme reagent for measuring cholesterol. In the reagent layer 3, the reaction layer 4 contains the surfactant for solubilizing cholesterol, and the detection layer 5 contains the enzyme reagent for measuring cholesterol.

Figure 5A:
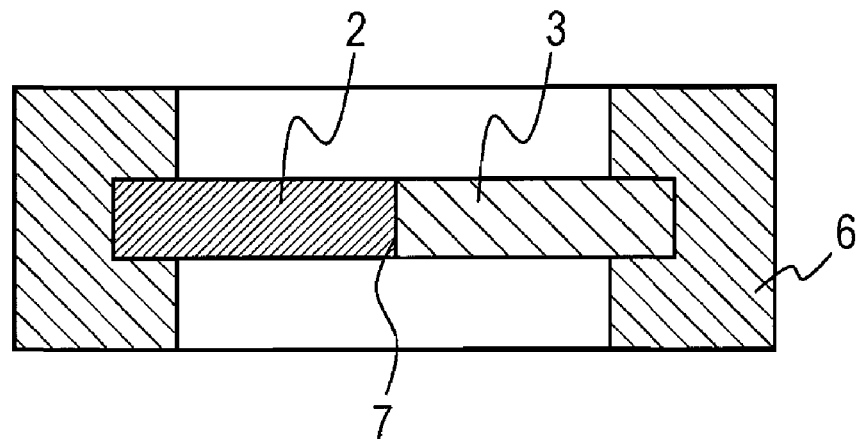
FIG. 5(A) is a cross-sectional view of still another example of the test piece of the present invention.
Figure 5B:
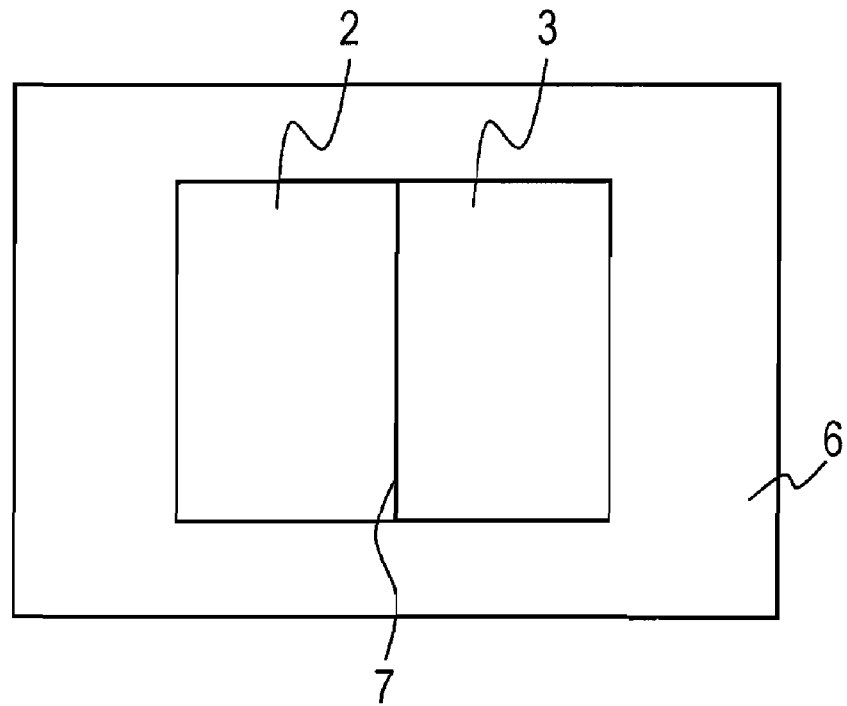
FIG. 5(B) is a plan view of the test piece shown in FIG. 5(A).

FIG. 5(A) shows a cross-sectional view of still another example of the test piece of the present invention, and FIG. 5(B) shows a plan view of this example. In the test piece of this example, as with the test piece shown in FIG. 4, the test piece is divided perpendicularly in half by a boundary 7 relative to the surface to which a sample is applied, and one half and the other half are for use as a reagent layer 2 that serves as the non-LDL cholesterol measurement portion and a reagent layer 3 that serves as the total-cholesterol measurement portion, respectively. The outer edge of the test piece of this example is in a state of being fitted in a slot in an outer frame 6. The reagent layers 2 and 3 both may be provided with a reaction layer and a detection layer as with the test piece of FIG. 4. As described above, in the reagent layer 2, the reaction layer may be divided into an upper layer and a lower layer, and the upper layer may contain the surfactant for inhibiting LDL cholesterol dissolution and the LDL cholesterol agglomerating agent and the lower layer may contain the surfactant for solubilizing non-LDL cholesterol. Otherwise, the test piece is identical to the test piece shown in FIG. 1 above and is used in the same manner. The detection layer of the reagent layer 2 contains the enzyme reagent for cholesterol measurement. In the reagent layer 3, the reaction layer may contain the surfactant for solubilizing cholesterol and the detection layer may contain the enzyme reagent for measuring cholesterol.

In addition, in the test piece of the present invention, a blood cell separation layer may be formed on the reagent layers. This may be accomplished by providing a porous member that is capable of filtering blood cells and by optionally providing a reflection layer. For example, a known blood cell separation material such as a glass filter can be used as the porous member. Thus, with a test piece that is provided with a blood cell separation layer, LDL cholesterol in plasma or serum can be measured simply by supplying whole blood as is.

As described above, the measurement method of the present invention is applicable also as a measurement method for use in a liquid system. This liquid-system measurement method can be performed, for example, using a first reaction vessel that serves as a total-cholesterol measurement portion and a second reaction vessel that serves as a non-LDL cholesterol measurement portion. The reaction vessels are not limited and examples include cuvettes, test tubes, etc.

In the liquid-system measurement method, a preferable configuration is such that:

in the step (A), the first reaction vessel contains the enzyme reagent for measuring cholesterol, and the second reaction vessel contains the enzyme reagent for measuring cholesterol, the surfactant for solubilizing non-LDL cholesterol and the surfactant for inhibiting LDL cholesterol dissolution;

in the step (B), the total cholesterol is measured with the enzyme reagent for measuring cholesterol; and in the step (C), due to the actions of the surfactant for solubilizing non-LDL cholesterol and the surfactant for inhibiting LDL cholesterol dissolution, non-LDL cholesterol is selectively measured by the enzyme reagent for measuring cholesterol. Moreover, a more preferable configuration is such that the second reaction vessel contains the LDL cholesterol agglomerating agent. In the liquid-system measurement method, those described above as measuring reagents can be used, such as the enzyme reagent for measuring cholesterol, the surfactant for solubilizing non-LDL cholesterol, the surfactant for inhibiting LDL cholesterol dissolution and the LDL cholesterol agglomerating agent. Measurement techniques are not particularly limited and examples include those that electrochemically or chemically measure hydrogen peroxide that is produced when the enzyme reagent is used. When a chemical measurement cannot be used due to the generation of turbidity in a reaction fluid, for example, when the LDL cholesterol agglomerating agent is used, it is preferable to employ an electrochemical measurement that uses an enzyme electrode or the like.

Examples

Next, examples shall be described together with comparative examples. Below, the "K/S value" is a variable calculated using the following formula, and is used when converting reflectivity (R) into concentration.

$$K/S = (1-R)^2 / 2R \qquad \text{(Formula)}$$

Example 1

(A) Preparation of Non-LDL Cholesterol Measurement Portion

First, a solution having a composition as presented below for forming a detection layer was applied to a support plate made of a white PET film (thickness: 125 μm) so as to attain a thickness of 150 μm and then dried at 40° C. for 10 minutes, thereby giving a detection layer. Meanwhile, a knitted polyethylene fabric (thickness: 250 μm) was impregnated with a first liquid reagent having a composition as presented below and then dried at 40° C. for 10 minutes. A second liquid reagent having a composition as presented below was applied to one surface of the knitted polyethylene fabric and then dried at 40° C. for 10 minutes, thereby giving a sample supply layer. Next, a liquid for lamination was sprayed over a surface of the detection layer. Then, the sample supply layer was laminated on the detection layer on which the liquid for lamination had been sprayed such that the surface to which the second liquid reagent had been applied faced upward, which was then dried at 40° C. for 10 minutes, thereby giving a non-LDL cholesterol measurement portion. The concentration of each component shown in the compositions presented below refers to the ratio upon sample application, i.e. the final concentration when 5 μL of a sample was supplied (concentration upon enzymatic reaction).

| Component | Concentration |
|---|---|
| Composition of Solution for Forming Detection Layer | |
| POD (manufactured by Toyobo Co., Ltd.) | 764 U/mL |
| 4-Aminoantipyrine (manufactured by Kishida Chemical Co., Ltd.) | 43 mmol/L |
| DAOS (manufactured by Dojindo Laboratories) | 51 mmol/L |
| TES buffer (manufactured by Dojindo Laboratories, pH 7.7) | 300 mmol/L |
| Composition of First Liquid Reagent | |
| TES buffer (manufactured by Dojindo Laboratories, pH 7.7) | 30 mmol/L |
| Cholesterol esterase | 46 U/mL |
| Cholesterol oxidase | 35 U/mL |
| Polyoxyethylene alkylene tribenzyl phenyl ether (manufactured by Kao Corporation, trade name: Emulgen B66) | 5 wt % |
| Composition of Second Reagent Solution | |
| Polyoxyethylene-polyoxypropylene condensation product (manufactured by ADEKA Corporation, trade name: Pluronic F-88) | 4 wt % |
| Potassium polyvinyl sulfate | 0.10 wt % |
| Polyglycol methyl ether | 5 wt % |
| Composition of Liquid for Lamination | |
| Distilled water | 100 wt % |

(B) Preparation of Total-Cholesterol Measurement Portion

Furthermore, a solution having a composition as presented below for forming a detection layer was applied to the support plate at a place adjacent to the non-LDL cholesterol measurement portion so as to attain a thickness of 150 μm and then dried at 40° C. for 10 minutes, thereby giving a detection layer. Meanwhile, a liquid for lamination having a composition as presented below was sprayed over a knitted polyethylene fabric (thickness: 250 μm). Then, the knitted polyethylene fabric that had been sprayed with the liquid for lamination was laminated on the detection layer, which was dried at 40° C. for 10 minutes, thereby giving a total-cholesterol measurement portion and, thus, the test piece of this example was prepared. The concentration of each component shown in the compositions presented below refers to the ratio upon sample application, i.e. the final concentration when 5 μL of a sample was supplied (concentration upon enzymatic reaction).

| Component | Concentration |
|---|---|
| Composition of Solution for Forming Detection Layer | |
| Phosphate buffer (pH 7.5) | 90 mmol/L |
| Cholesterol esterase | 795 U/mL |
| Cholesterol oxidase | 233 U/mL |
| POD | 750 U/mL |
| 4-Aminoantipyrine (manufactured by Kishida Chemical Co., Ltd.) | 44 mmol/L |
| DAOS (manufactured by Dojindo Laboratories) | 53 mmol/L |
| Composition of Liquid for Lamination | |
| Phosphate buffer (pH 7.5) | 17 mmol/L |
| Sodium deoxycholate | 0.5 wt % |

Example 2

The test piece of Example 2 was prepared in the same manner as in Example 1 except that the final concentration of potassium polyvinyl sulfate in the non-LDL cholesterol measurement portion upon sample application (ratio relative to the total components upon sample application) was 0.05 wt %.

Example 3

The test piece of Example 3 was prepared in the same manner as in Example 1 except that the non-LDL cholesterol measurement portion contained neither potassium polyvinyl sulfate nor polyglycol methyl ether.

Examination of Correlation with Known Concentration

Using the test pieces obtained in Examples 1 to 3, LDL cholesterol levels of 55 serum samples whose LDL cholesterol levels were already known were measured. The LDL cholesterol levels were measured as follows. That is, first, 5 μL of a blood sample was dripped over both the total-cholesterol measurement portion and the non-LDL cholesterol measurement portion of each test piece. The reflectance of each measurement portion then was measured with a special-purpose reflectometer (trade name: Spotchem, manufactured by ARKRAY Inc.). In the measurement, the measurement wavelength was 610 nm. Then, based on the reflectance thus measured, LDL cholesterol levels (K/S values) were obtained. Then, a correlation coefficient between the LDL cholesterol level of each test piece that was obtained from actual measurement and known concentrations was calculated. The results are shown in Table 1 below.

TABLE 1

| Examples | Potassium polyvinyl sulfate concentration (wt %) | Correlation coefficient (r) |
|---|---|---|
| Example 1 | 0.10 | 0.9651 |
| Example 2 | 0.05 | 0.9640 |
| Example 3 | 0.00 | 0.9457 |

As shown in Table 1, the LDL cholesterol levels measured using the test pieces of Examples 1 to 3 exhibited high correlation coefficients with the previously known concentration. In particular, very high correlation coefficients were obtained with the test pieces of Example 1 and Example 2 that contained potassium polyvinyl sulfate.

Examination of K/S Values Over Time

Figure 6:
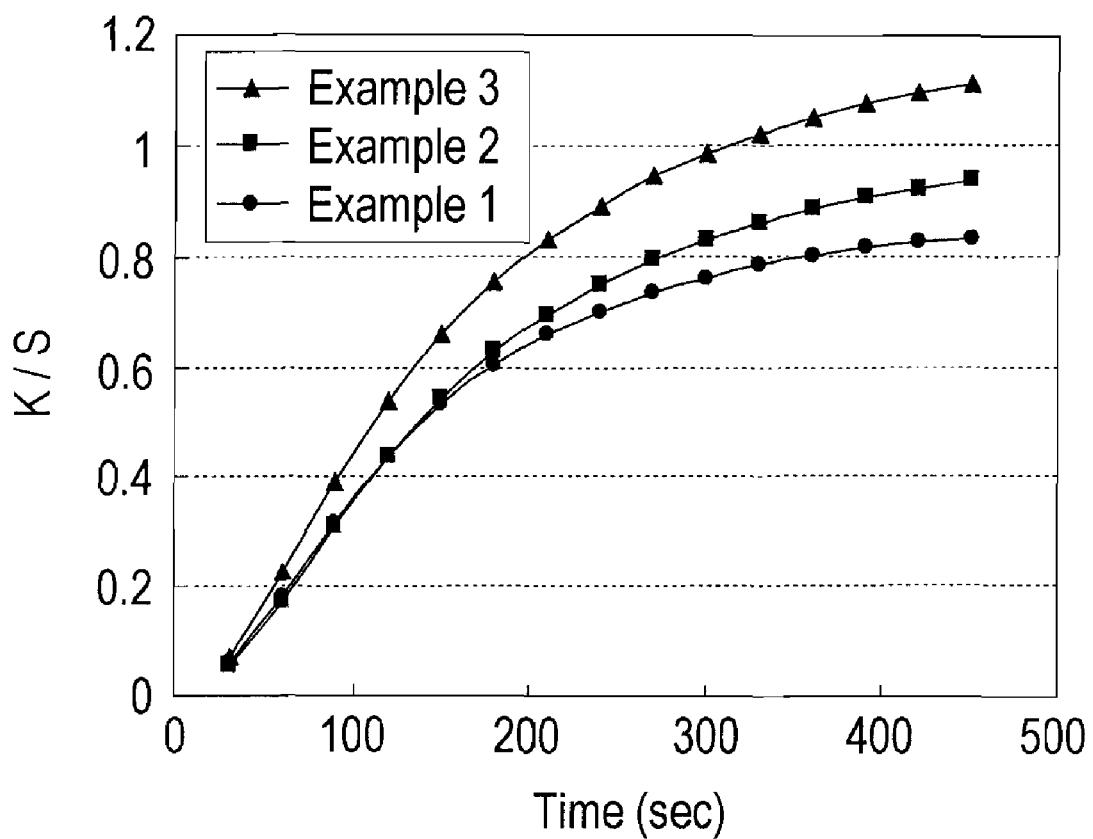
FIG. 6 is a graph showing the K/S values over time in connection with an example of the measurement method of the present invention.

FIG. 6 is a graph showing the LDL cholesterol levels (K/S values) over time obtained with the test pieces of Examples 1 to 3. In the graph of FIG. 6, the horizontal axis indicates a measurement time (sec) and the vertical axis indicates a K/S value as described above. Moreover, in the graph of FIG. 6, circles indicate the results of Example 1, squares indicate the results of Example 2 and triangles indicate the results of Example 3.

As shown in the graph of FIG. 6, in the measurement of LDL cholesterol levels using the test pieces of Examples 1 to 3, the reaction reached its end point in each case. Therefore, in the measurement using the test pieces of Examples 1 to 3, the reaction of LDL cholesterol was inhibited and only the non-LDL cholesterol reacted, and it was thus possible to measure LDL cholesterol levels highly precisely. Moreover, in the measurement using the test pieces of Examples 1 and 2 containing potassium polyvinyl sulfate, K/S values were further lower and only the non-LDL cholesterol reacted, and it was thus possible to measure LDL cholesterol levels more precisely.

Comparison with Dried Test Piece Made from Liquid Reagent

Comparative Example 1

In Comparative Example 1, a liquid reagent for measuring LDL cholesterol (wet chemistry) for use with the direct method was dried as a test piece with reference to the composition of a reagent in Example 1 of Patent Document 1 (JP 3091230B). The test piece of Comparative Example 1 was prepared by impregnating a knitted polyethylene fabric (250 µm) with a liquid reagent having a composition as presented below, followed by drying at 40° C. for 10 minutes. The concentration of each component in the composition presented below refers to the final concentration when 5 µL of a sample was supplied (concentration upon enzymatic reaction).

| Composition of Liquid Reagent | |
|---|---|
| Component | Concentration |
| α-Cyclodextrin | 5 mmol/L |
| Polyoxyethylene monolaurate | 0.5 wt % |
| Cholesterol esterase | 0.25 U/mL |
| Cholesterol oxidase | 1.25 U/mL |
| POD | 6.25 U/mL |
| 4-Aminoantipyrine | 0.55 mmol/L |
| DAOS | 0.83 mmol/L |
| Tris-HCl buffer (pH 7.0) | 30 mmol/L |

Although EMSE (N-ethyl-N-(3-methylphenyl)-N'-succinyl-ethylenediamine) is used as a color former in Example 1 of Patent Document 1, DAOS (N-ethyl-N-(2-hydroxy-3-sulfopropyl)-3,5-dimethoxyaniline) was used instead in Comparative Example 1.

Figure 7:
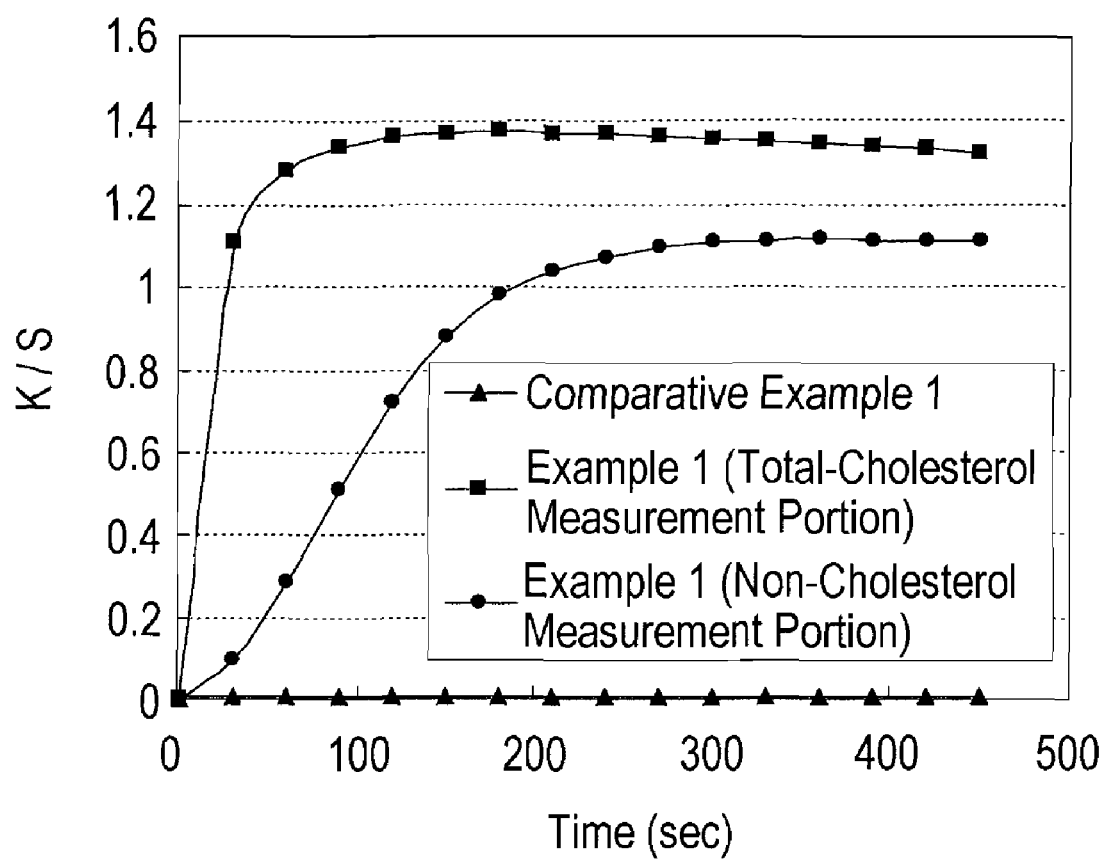
FIG. 7 is a graph showing the K/S values over time in connection with a comparative measurement method and an example of the measurement method of the present invention.

With respect to the test pieces of Comparative Example 1 and Example 1 thus obtained, the reflectivity (over time) of each measurement portion of the test pieces was measured in the same manner as above using a control serum that had a known concentration as a specimen, and the LDL cholesterol levels (K/S values) were obtained. The results are shown in the graph of FIG. 7. In the graph of FIG. 7, the horizontal axis indicates a measurement time (sec) and the vertical axis indicate a K/S value as described above. Moreover, in the graph of FIG. 7, squares indicate the results for the total-cholesterol measurement portion of Example 1, circles are for the non-LDL cholesterol measurement portion of Example 1, and triangles indicate the results of a measurement with the test piece of Comparative Example 1.

As is clear from the graph of FIG. 7, reaction in the total-cholesterol measurement portion of Example 1 and the non-LDL cholesterol measurement portion of Example 1 reached the end point. Therefore, it can be understood that in the measurement portions of the test piece of Example 1, measurement of anything other than the measurement targets was prevented, allowing the total-cholesterol measurement portion to measure only the total cholesterol and the non-LDL cholesterol measurement portion to measure only the non-LDL cholesterol. In contrast, with the test piece of Comparative Example 1 prepared by drying a liquid reagent for LDL cholesterol measurement that is for use in a liquid system, no reaction occurred and measurement of LDL cholesterol thus failed. Accordingly, it can be understood that, as described above, the measurement of LDL cholesterol cannot be performed simply by drying a liquid reagent for LDL cholesterol measurement.

Comparison of Accuracy of Measured Values with Those of Liquid Reagent

Example 4

The test piece of Example 4 was prepared in the same manner as in Example 1 except that a non-LDL cholesterol measurement portion was formed such that the final concentration of polyoxyethylene alkylene tribenzyl phenyl ether was 7.5 wt %.

Comparative Example 2

For Comparative Example 2, a serum LDL cholesterol measurement kit (trade name "Cholestest LDL", manufactured by Sekisui Medical Co., Ltd.) that is a liquid reagent for LDL cholesterol measurement for use with the elimination method was used.

Figure 8:
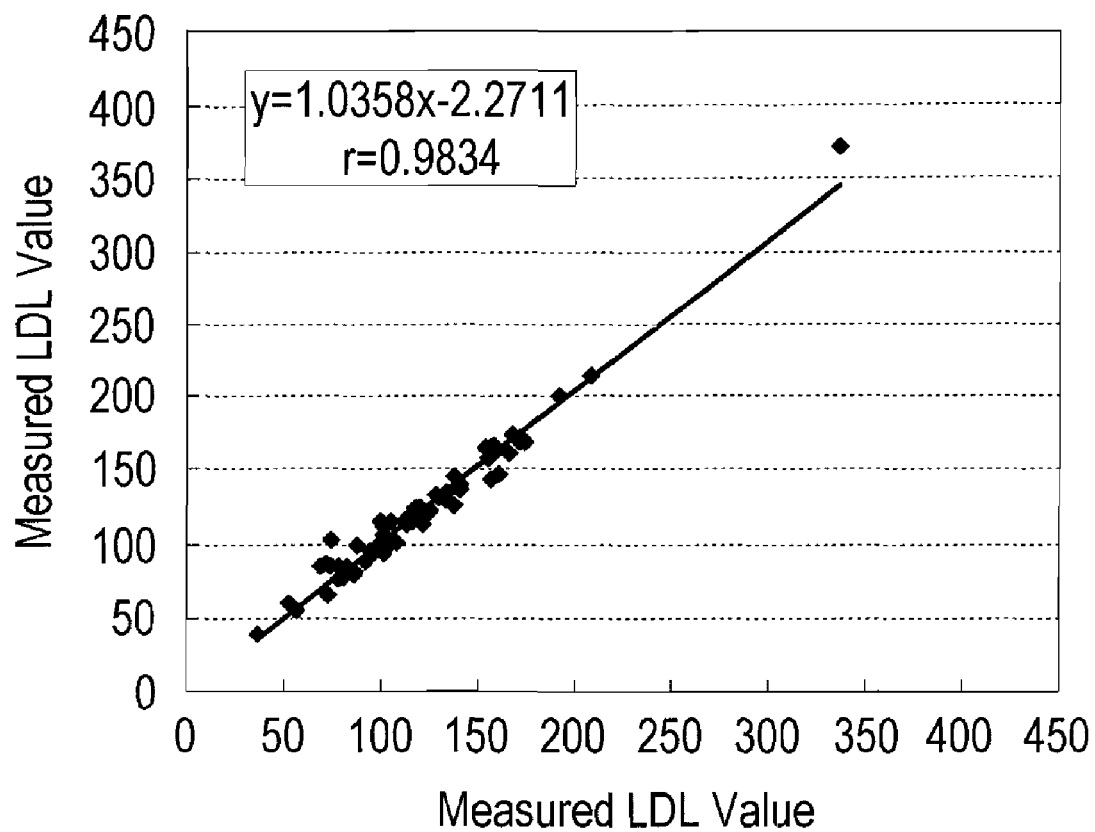
FIG. 8 is a graph showing the correlation between the values measured in another example of the measurement method of the present invention and the values measured in another comparative measurement method.

Using the test pieces of Example 4 and Comparative Example 2 thus obtained, the LDL cholesterol levels of 70 serum samples were measured. In the measurements using the test piece of Example 4, reflectivity was measured as described above and LDL cholesterol levels (K/S values) were then obtained. On the other hand, in the measurements of Comparative Example 2 using a commercially available measurement kit, the absorbance of a reaction fluid after a color reaction was measured using an absorption spectrometer, and LDL cholesterol levels were then obtained. Thereafter, the correlation between the values measured in Example 4 and the values measured in Comparative Example 2 was investigated. The results are shown in the graph of FIG. 8. In the graph of the FIG. 8, the vertical axis is for the values measured in Example 4, and the horizontal axis is for the values measured in Comparative Example 2.

As shown in the graph of FIG. 8, there was a good correlation between the values measured in Example 4 and the values measured in Comparative Example 2, with the correlation coefficient thereof being r=0.9834. It therefore was demonstrated that the test piece of the present invention can measure LDL cholesterol levels with accuracy equal to or greater than that of a commercially available serum LDL cholesterol kit. Although the reagent of Comparative Example 2 was liquid and required large amounts of rinsing water, which generated liquid waste during measurement, the test piece of Example 4 did not require rinsing water and, naturally, liquid waste was not generated, thereby allowing measurement to be performed conveniently.

Example 5

In Example 5, a test piece was prepared in the same manner as in Example 1 except that a non-LDL cholesterol measurement portion was formed with the use of a solution for forming a detecting layer, a first liquid reagent and a liquid for lamination all having the following compositions and no second liquid reagent was applied to a surface of a knitted polyethylene fabric as used above.

| Component | Concentration |
|---|---|
| Composition of Solution for Forming Detection Layer | |
| POD (manufactured by Toyobo Co., Ltd.) | 764 U/mL |
| 4-Aminoantipyrine (manufactured by Kishida Chemical Co., Ltd.) | 43 mmol/L |

-continued

| Component | Concentration |
|---|---|
| DAOS (manufactured by Dojindo Laboratories) | 51 mmol/L |
| TES buffer (manufactured by Dojindo Laboratories, pH 7.7) | 300 mmol/L |
| Composition of First Liquid Reagent | |
| Polyoxyethylene-polyoxypropylene condensation product (manufactured by ADEKA, trade name: Pluronic F88) | 4 wt % |
| Composition of Liquid for Lamination | |
| TES buffer (manufactured by Dojindo Laboratories, pH 7.7) | 30 mmol/L |
| Cholesterol esterase | 46 U/mL |
| Cholesterol oxidase | 35 U/mL |
| Polyoxyethylene alkylene tribenzyl phenyl ether (manufactured by Kao Corporation, trade name Emulgen B66) | 5 wt % |

Figure 9:
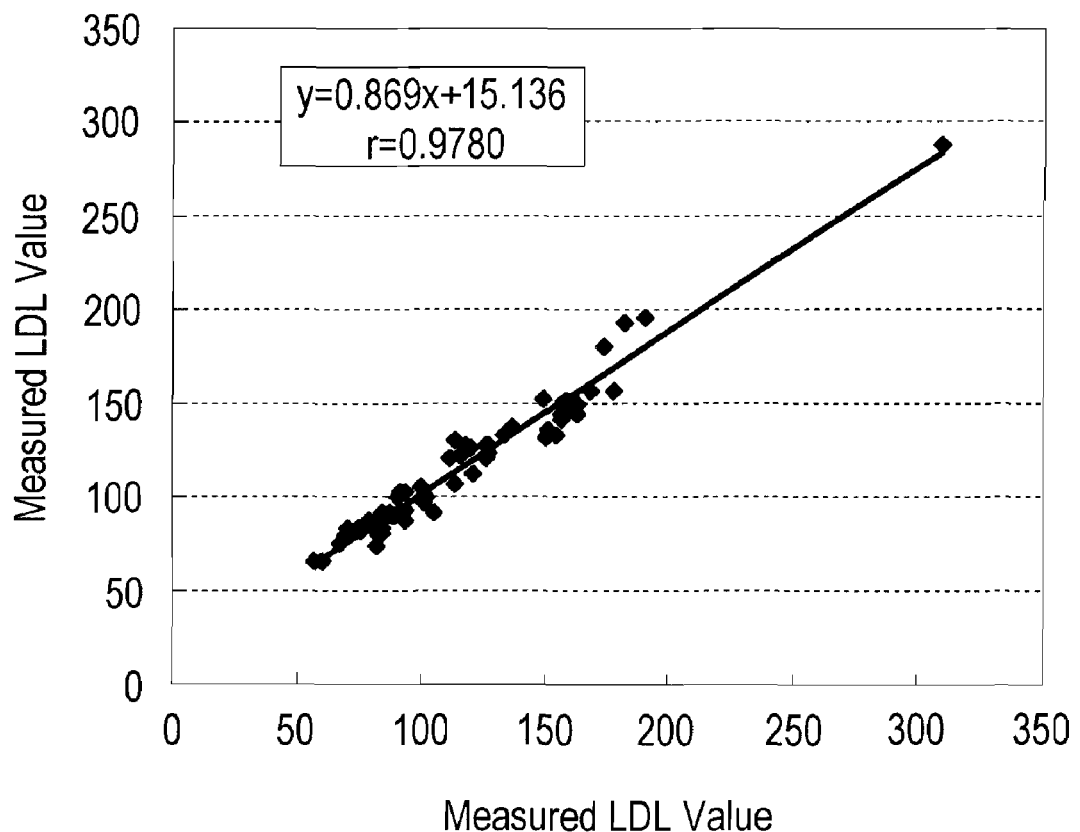
FIG. 9 is a graph showing the correlation between the values measured in still another example of the measurement method of the present invention and the values measured in still another comparative measurement method.

Using the test pieces of Example 5 and Comparative Example 2 thus obtained, LDL cholesterol levels of 61 serum samples were measured. In the measurements using the test piece of Example 5, reflectivity was measured as described above and LDL cholesterol levels (K/S values) were then obtained. On the other hand, in the measurement of Comparative Example 2 using a commercially available measurement kit, absorbance was measured as described above and LDL cholesterol levels were then obtained. Thereafter, the correlation between the values measured in Example 5 and the values measured in Comparative Example 2 was investigated. The graph of FIG. 9 shows the correlation between the values measured in Example 5 and the values measured in Comparative Example 2. In the graph of the FIG. 9, the vertical axis is for the values measured in Example 5, and the horizontal axis is for the values measured in Comparative Example 2.

As shown in the graph of FIG. 9, there was a good correlation between the values measured in Example 5 and the values measured in Comparative Example 2, with the correlation coefficient thereof being r=0.9780. It was therefore demonstrated that the test piece of Example 5 can measure LDL cholesterol levels with accuracy equal to or greater than that of a commercially available serum LDL cholesterol kit. Although the reagent of Comparative Example 2 was liquid and required large amounts of rinsing water, which generated liquid waste during measurement, the test piece of Example 5 did not require rinsing water, and naturally, liquid waste was not generated, thereby allowing measurement to be performed conveniently.

INDUSTRIAL APPLICABILITY

Using the test piece for measuring LDL cholesterol of the present invention, the measurement of LDL cholesterol can be performed with a small measurement device of a simple structure. Therefore, the test piece for measuring LDL cholesterol of the present invention is of application in a broad range of technical fields, for example, it is of use in technical fields where a large number of specimens need to be subjected to measurement, such as clinical examinations.

The invention claimed is:

1. A method for measuring low-density lipoprotein (LDL) cholesterol in a sample using a test piece comprising
    a total-cholesterol measurement portion, which comprises
        an enzyme reagent for measuring cholesterol, and
    a non-LDL cholesterol measurement portion, which comprises
        an enzyme reagent for measuring cholesterol,
        a surfactant for solubilizing non-LDL cholesterol,
        a surfactant for inhibiting LDL cholesterol dissolution, and
        a LDL cholesterol agglomerating agent,
    the method comprising steps (A) to (C):
    (A) measuring total cholesterol in the sample in the total-cholesterol measurement portion of the test piece;
    (B) measuring selectively non-LDL cholesterol in the sample in the non-LDL cholesterol measurement portion of the test piece; and
    (C) obtaining an LDL cholesterol level of the sample by subtracting the non-LDL cholesterol value measured in the step (B) from the total-cholesterol value measured in the step (A),
    wherein a portion for measuring total cholesterol and a portion for measuring non-LDL cholesterol are provided on the same test piece; and
    wherein in the step (B), the non-LDL cholesterol is selectively measured by the enzyme reagent for measuring cholesterol, wherein the surfactant for solubilizing non-LDL cholesterol solubilizes the non-LDL cholesterol, the surfactant for inhibiting LDL cholesterol dissolution inhibits LDL cholesterol dissolution and the LDL cholesterol agglomerating agent agglomerates the LDL cholesterol.

2. The method according to claim 1, wherein the surfactant for solubilizing non-LDL cholesterol comprises
    at least one surfactant selected from the group consisting of polyoxyethylene alkylene phenyl ethers and polyoxyethylene alkylene tribenzyl phenyl ethers; and
    the surfactant for inhibiting LDL cholesterol dissolution comprises at least one surfactant selected from the group consisting of polyoxyethylene alkyl ethers, polyoxyethylene alkyl phenyl ethers, polyoxyethylene-polyoxypropylene condensation products, polyoxyethylene alkyl ether sulfate salts and alkylbenzene sulfonate salts.

3. The method according to claim 1, wherein the enzyme reagent comprises a cholesterol esterase and a cholesterol oxidase.

4. The method according to claim 1, wherein the enzyme reagent comprises a cholesterol esterase and a cholesterol dehydrogenase.

5. The method according to claim 1, wherein the LDL cholesterol agglomerating agent is a polyvinyl sulfate salt.

6. The method according to claim 1, wherein the test piece comprises a support, a first reagent layer, and a second reagent layer,
    the first reagent layer and the second reagent layer being disposed on the support,
    wherein the first reagent layer comprises the total-cholesterol measurement portion, and
    wherein the second reagent layer comprises the non-LDL cholesterol measurement portion.

7. The method according to claim 1, wherein the test piece comprises a first support, a second support, a first reagent layer, and a second reagent layer,
    the first reagent layer being disposed on the first support,
    the second reagent layer being disposed on the second support,
    wherein the first reagent layer comprises the total-cholesterol measurement portion and
    wherein the second reagent layer comprises the non-LDL cholesterol measurement portion.

8. The method according to claim 1, wherein the non-LDL cholesterol is high-density lipoprotein (HDL) cholesterol and very-low-density lipoprotein (VLDL) cholesterol.

* * * * *